United States Patent
Jadwizak et al.

(10) Patent No.: US 10,965,082 B2
(45) Date of Patent: Mar. 30, 2021

(54) PLUG WITH AN OVER-MOLDED, NON-ROTATABLE PLUG CONNECTOR AND FOUR CONNECTORS, IN PARTICULAR AN IS4/DF4 PLUG

(71) Applicant: BIOTRONIK SE & Co. KG, Berlin (DE)

(72) Inventors: Detmar Jadwizak, Erkner (DE); Dajana Kaiser, Berlin (DE); Carsten Fruendt, Berlin (DE); Gordon Hillebrand, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 16/560,403

(22) Filed: Sep. 4, 2019

(65) Prior Publication Data

US 2020/0106232 A1  Apr. 2, 2020

(30) Foreign Application Priority Data

Oct. 2, 2018 (DE) .......................... 102018124307.3

(51) Int. Cl.
| | | |
|---|---|---|
| H01R 43/24 | (2006.01) | |
| H01R 24/58 | (2011.01) | |
| H01R 24/38 | (2011.01) | |
| H01R 13/46 | (2006.01) | |
| H01R 13/52 | (2006.01) | |
| H01R 107/00 | (2006.01) | |

(52) U.S. Cl.
CPC ............ *H01R 43/24* (2013.01); *H01R 13/465* (2013.01); *H01R 24/38* (2013.01); *H01R 24/58* (2013.01); *H01R 13/5224* (2013.01); *H01R 2107/00* (2013.01); *H01R 2201/12* (2013.01)

(58) Field of Classification Search
CPC ...... H01R 43/24; H01R 13/465; H01R 24/38; H01R 24/58
USPC ........................................................ 439/488
See application file for complete search history.

(56) References Cited

U.S. PATENT DOCUMENTS

| | | | | |
|---|---|---|---|---|
| 2,946,978 A | * | 7/1960 | Cook | H01R 24/58 439/460 |
| 5,139,444 A | * | 8/1992 | Garay | H01R 24/58 439/668 |
| 7,083,474 B1 | * | 8/2006 | Fleck | A61N 1/3752 439/218 |

(Continued)

OTHER PUBLICATIONS

German Search Report for German Case No. DE 10 2018 124 307.3, dated Jun. 19, 2019 (9 pages).

*Primary Examiner* — Alexander Gilman
(74) *Attorney, Agent, or Firm* — Buchanan Ingersoll & Rooney PC

(57) ABSTRACT

A method for producing a plug, and to a plug. It is provided, in particular, that a plug connector and three plug contact rings are arranged in a casting mold, wherein the plug connector extends along a longitudinal axis and has a contact portion and a fastening portion connected integrally to the contact portion, and wherein a plug housing is formed by introducing a casting material into the casting mold so that the fastening portion is surrounded form-fittingly by the casting material and the contact portion protrudes out from the plug housing at a first end of the plug housing in the direction of the longitudinal axis.

10 Claims, 6 Drawing Sheets

(56) References Cited

U.S. PATENT DOCUMENTS

| | | | |
|---|---|---|---|
| 7,175,478 B2* | 2/2007 | Ollivier | H01R 13/5224 439/669 |
| 7,241,180 B1* | 7/2007 | Rentas Torres | A61N 1/05 439/668 |
| 8,382,529 B2* | 2/2013 | Lim | H01R 24/58 439/669 |
| 8,641,436 B2* | 2/2014 | Regnier | A61N 1/05 439/218 |
| 8,914,110 B2* | 12/2014 | He | A61N 1/3758 607/36 |
| 9,327,133 B2* | 5/2016 | Rutten | A61N 1/375 |
| 9,537,259 B2* | 1/2017 | Mastel | H01R 13/639 |
| 9,716,343 B2* | 7/2017 | Wess | H01R 13/645 |
| 9,935,449 B1* | 4/2018 | Kruger | H02G 15/043 |
| 2009/0203258 A1* | 8/2009 | Guenther | H01R 24/58 439/587 |
| 2009/0280697 A1* | 11/2009 | Li | B29C 45/1671 439/736 |
| 2010/0210146 A1* | 8/2010 | Jang | B29C 45/1459 439/638 |
| 2012/0151765 A1* | 6/2012 | James, IV | H01R 43/20 29/882 |
| 2014/0213118 A1* | 7/2014 | Glynn | A61N 1/0563 439/675 |
| 2015/0165216 A1* | 6/2015 | Hughes | A61N 1/3752 439/626 |

\* cited by examiner

PLUG WITH AN OVER-MOLDED, NON-ROTATABLE PLUG CONNECTOR AND FOUR CONNECTORS, IN PARTICULAR AN IS4/DF4 PLUG

CROSS-REFERENCE TO RELATED APPLICATIONS

This patent application claims the benefit of and priority to co-pending German Patent Application No. DE 10 2018 124 307.3 filed on Oct. 2, 2018 in the German Patent Office, which is hereby incorporated by reference in its entirety

TECHNICAL FIELD

The present invention relates to a plug, in particular for a medical implant, in particular an IS4/DF4 plug, and to a method for producing such a plug.

BACKGROUND

Plugs of this kind are disclosed, for example, in U.S. Publication No. 2010/0210146 and in U.S. Publication No. 2015/0165216. In U.S. Publication No. 2010/0210146, circumferential plug contact rings, for example, are contacted with a cable each, which extends through the plug body, wherein the plug connector by contrast is contacted via a helical conductor, which can extend in a central lumen of the plug connector.

Furthermore, in U.S. Publication No. 2015/0165216 A1 as well, the plug connector is contacted via a conductive core, which is connected to a separate plug connector.

The present invention is directed at overcoming one or more of the above-mentioned problems.

SUMMARY

Proceeding here from, an object of the present invention is to create a method for producing a plug of the kind described in the introduction and also such a plug that has a comparatively simple design and, in particular, allows particularly simple electrical attachment to the plug, for example, in the case of use of a coradial coil or a 4-wire system.

At least this object is achieved by a method for producing a plug having the features of claim 1 and by a plug having the features of claim 10 and of claim 11. Advantageous embodiments of the individual aspects of the present invention are specified in the corresponding dependent claims and will be described hereinafter.

According to claim 1, a method for producing a plug is disclosed, in particular an IS4/DF4 plug, wherein a plug connector and three plug contact rings are arranged in a casting mold, wherein the plug connector extends along a longitudinal axis and has a contact portion and a fastening portion connected integrally to the contact portion, and wherein a plug housing is formed by introducing a casting material into the casting mold so that the fastening portion is surrounded form-fittingly by the casting material and the contact portion protrudes out from the plug housing at a first end of the plug housing in the axial direction.

Inclusive of electrical attachments of the plug contact rings and of the plug connector, the plug therefore advantageously has only four components that are to be arranged in the casting mold, wherein in particular the casting material can be cast over or molded around said components to form the plug housing and in order to fix the components to one another.

The fastening portion of the plug connector is preferably hereby integrally connected to the contact portion. Within the scope of the present invention this means, in particular, that the plug connector forms a monolithic body comprising the contact portion and the fastening portion, which monolithic body is cast or extruded as a cohesive unit, is milled from solid material, or is otherwise formed into a monolithic body. In particular, the contact portion in accordance with one embodiment has a homogeneous structure. In particular, the plug connector—in contrast to the prior art—is not formed by an integrally bonded connection of two or more separate bodies (for example, by joining, in particular welding, a separate contact portion to a separate fastening portion), but is preferably provided or formed from the outset as an individual, cohesive body.

In accordance with an embodiment of the method, it is provided that the fastening portion and the three plug contact rings are electrically conductively connected (in particular in each case by way of a welded or a soldered connection) to a first end portion of an electrical conductor each, prior to the introduction of the casting material (and in particular prior to the insertion of the plug connector) into the casting mold, wherein each conductor has a second end portion, which forms a contact of the plug in order to electrically contact the corresponding conductor.

Furthermore, it is provided in accordance with an embodiment of the method that the four conductors are enclosed in the plug housing by the introduction of the casting material into the casting mold, so that the second end portions or contacts of the conductors protrude out from the plug housing at a second end of the plug housing.

In accordance with a further embodiment of the method, it is provided that the second end portion of each conductor extends along the longitudinal axis, wherein the second end portions preferably each are arranged at the same distance from the longitudinal axis of the plug connector in a radial direction running perpendicularly to the longitudinal axis.

The present invention thus advantageously makes it possible for all four conductors or contacts thereof to lie over the same radius and therefore to be contacted identically.

In accordance with a further embodiment of the method, it is provided that the plug contact rings each have an outer side, wherein the plug housing is formed by introducing the casting material into the casting mold such that the outer sides of the plug contact rings are each arranged in an exposed manner on an outer side of the plug housing. Here, the outer sides of the plug contact rings can be formed flush with an outer side of the plug housing.

It is furthermore provided in accordance with an embodiment of the method, that each conductor electrically conductively connected to a plug contact ring is electrically conductively connected via the first end portion to an inner side of the plug contact ring. In particular, the plug contact rings and the plug connector are electrically insulated from one another by the plug housing.

It is furthermore provided in accordance with an embodiment of the method, that, in order to form a protrusion of the plug housing at the second end of the plug housing, which protrusion is extended along the longitudinal axis, and/or in order to form an inner lumen of the plug housing extending along the longitudinal axis, an appropriate core is arranged in the casting mold prior to the introduction of the casting material into the casting mold.

The protrusion produced in this way, which, in particular, surrounds an end portion of the inner lumen, is also referred to as a heel and is designed to shield the contacts of the conductors provided at the end portions against liquid in the inner lumen of the plug or plug housing. Once the casting material has cured, the core can be removed in order to clear the inner lumen.

Said protrusion can have a cylindrical first portion and a second portion connected to the first portion, wherein the second portion has four side walls, wherein each side wall is opposite second end portion or contact of a conductor. Said side walls of the second portion can be straight, concave or convex.

It is furthermore provided in accordance with an embodiment of the method, that the plug connector also surrounds a lumen which is fluidically connected to the inner lumen of the plug housing once the plug housing has been formed and in particular is aligned therewith. The plug thus has a continuous lumen for receiving a guide wire or a mandrel.

It is furthermore provided in accordance with an embodiment of the method, that the plug housing is cast from the casting material such that the plug housing has a coding for distinguishing between the conductors or the contacts of the conductors. The coding can be formed at a circumferential edge of an end face of the plug housing, wherein it protrudes from the end face of said protrusion of the plug housing. The coding is preferably formed on said edge by a flattened portion of the plug housing, which flattened portion can be predefined by the casting mold. Alternatively, the coding can also be formed by a groove or an elevation, for example in the form of a point.

It is furthermore provided in accordance with an embodiment of the method, that the casting material is one of the following materials: PEEK or another plastic, wherein the hardness of the particular plastic material is greater than 75 Shore D, and wherein the particular plastic material has a mean roughness (Ra) which is less than 0.8 μm.

The plug connector and/or the plug contact rings is/are preferably formed from one of the following materials or comprises/comprise one of the following materials: stainless steel, MP35N (composition defined in ASTM F562) platinum, platinum/iridium with a composition of 70 to 95% platinum and 5 to 30% iridium, gold, gold alloys.

In accordance with an embodiment of the method, the casting material is introduced into the casting mold by way of injection molding, wherein the casting material is injected into the casting mold under pressure in a liquefied state and the casting material transitions by cooling into the solid state and is then removed from the casting mold.

A further aspect of the present invention relates to a plug which has been produced by means of the method according to the invention.

The present invention furthermore relates to a plug comprising:
- a plug housing, which extends along the longitudinal axis,
- a plug connector extended along the longitudinal axis and which comprises a contact portion and a fastening portion connected integrally to the contact portion, wherein the fastening portion is cast form-fittingly in the plug housing so that the contact portion protrudes out from the plug housing at a first end of the plug housing in the direction of the longitudinal axis,
- three plug contact rings arranged coaxially with respect to the longitudinal axis, wherein the plug contact rings each have an outer side, and wherein the plug contact rings are cast (embedded) in the plug housing so that the outer sides of the plug contact rings are each arranged in an exposed manner on an outer side of the plug housing and are electrically contactable.
- wherein the fastening portion of the plug connector and the photo contact rings are electrically conductively connected to a first end portion of an electrical conductor each, wherein each conductor is cast in the plug housing and protrudes out from the plug housing at a second end of the plug housing via a second end portion, wherein the second end portion of each conductor forms a contact for electrically contacting the corresponding conductor, and wherein in particular the electrical conductor connected to the fastening portion of the plug connector is cast together with the fastening portion form-fittingly in the plug housing so that the plug connector is fixed in the plug housing non-rotatably with respect to a rotation about the longitudinal axis.

With regard to the term "integrally connected", reference is made to the comments above.

In accordance with an embodiment, the fastening portion can have a circumferential recess, so that the plug housing can engage in said recess. The plug connector, as a result, cannot be removed from the plug housing in the direction of the longitudinal axis.

In accordance with an embodiment of the plug, it is provided that the second end portion of each conductor extends in the direction of the longitudinal axis, wherein the end portions are each arranged at the same distance from the longitudinal axis of the plug connector in a radial direction running perpendicularly to the axial direction.

It is furthermore provided in accordance with an embodiment of the plug, that each conductor electrically conductively connected to a plug contact ring is electrically conductively connected via the first end portion to an inner side of the relevant plug contact ring.

Each conductor furthermore preferably has a middle portion, via which the first and the second end portion of the particular conductor are connected to one another. The first end portion of each conductor can be angled or curved in order to facilitate connection to the inner side of the associated plug contact ring or in order to facilitate connection to a circumferential outer side of the fastening portion of the plug connector.

It is preferably provided that the middle portion and the second end portion connected thereto of each conductor extend along the longitudinal axis, wherein, in particular, the middle portions of the conductors run parallel to one another, and wherein, in particular, the second end portions of the conductors run parallel to one another.

It is furthermore preferably provided that the conductors are arranged further inwardly in the radial direction than the plug contact rings (hereby facilitating an electrically conductive connection to the inner sides of the plug contact rings). The plug contact rings are arranged adjacently along the longitudinal axis, wherein, in particular, a first plug contact ring extends in the circumferential direction of the plug connector around the fastening portion of the plug connector and around the conductor that is electrically conductively connected via its first end portion to the inner side of the first plug contact ring.

It is furthermore provided, in particular, that a second plug contact ring, which is arranged along the longitudinal axis between the first plug contact ring and a third plug contact ring, extends around those conductors that are electrically conductively connected to the fastening portion of the plug connector, the first plug contact ring, or the second plug contact ring.

It is furthermore provided, in particular, that the third plug contact ring extends around all four conductors.

In accordance with a further embodiment of the plug, the plug connector protrudes via its fastening portion into the first plug contact ring and ends in the direction of the longitudinal axis between the first plug contact ring and the second plug contact ring. In other words, the plug connector does not protrude into the second or the third plug contact ring. This advantageously relatively short design of the plug connector in the direction of the longitudinal axis is possible by the contacting of the plug connector by means of the associated conductor, which at the same time causes the plug connector to be secured against a rotation with respect to the plug housing about the longitudinal axis (see above).

In accordance with a further embodiment of the plug, it is provided that the plug housing surrounds an inner lumen (for example, for receiving a guide wire or a mandrel), wherein the inner lumen is fluidically connected to a lumen of the plug connector, wherein, in particular, the lumen of the plug connector is aligned with the inner lumen.

In accordance with a further embodiment of the plug, it is provided that the plug housing has a protrusion formed at the second end of the plug housing, which protrusion surrounds an end portion of the inner lumen. The protrusion is designed in particular to shield the contacts of the conductors provided at the end portions against a liquid in the lumen of the plug or plug housing.

In accordance with a further embodiment of the plug, it is provided that the protrusion has a cylindrical first portion, which at the end face has an opening, via which the inner luman is accessible. Furthermore, the protrusion can have a second portion connected to the first portion, wherein the second portion has four side walls, wherein each side wall is opposite an end portion or contact of a conductor. Said side walls of the second portion can be straight, concave or convex.

In accordance with a further embodiment of the plug, it is provided that the plug housing has a coding for distinguishing between the conductors. The coding can be formed on a circumferential edge of an end face of the plug housing, wherein the coding protrudes from the end face of said protrusion of plug. The coding is preferably formed by a flattened portion of the plug housing on said edge. Alternatively, the coding can also be formed by a groove or an elevation, for example in the form of a point.

Lastly, a further aspect of the present invention relates to a medical implant, for example, an implantable electrode lead, which has a plug according to the present invention. By means of the plug, the implantable electrode lead can be attached to an active implant, for example, to an implantable cardiac pacemaker, an implantable cardioverter/defibrillator (ICD) or to an implantable neurostimulator.

Additional features, aspects, objects, advantages, and possible applications of the present invention will become apparent from a study of the exemplary embodiments and examples described below, in combination with the Figures, and the appended claims.

DESCRIPTION OF THE DRAWINGS

Further features, advantages and embodiments of the present invention will be explained hereinafter with reference to the Figures, in which.

DETAILED DESCRIPTION

Figure 1:
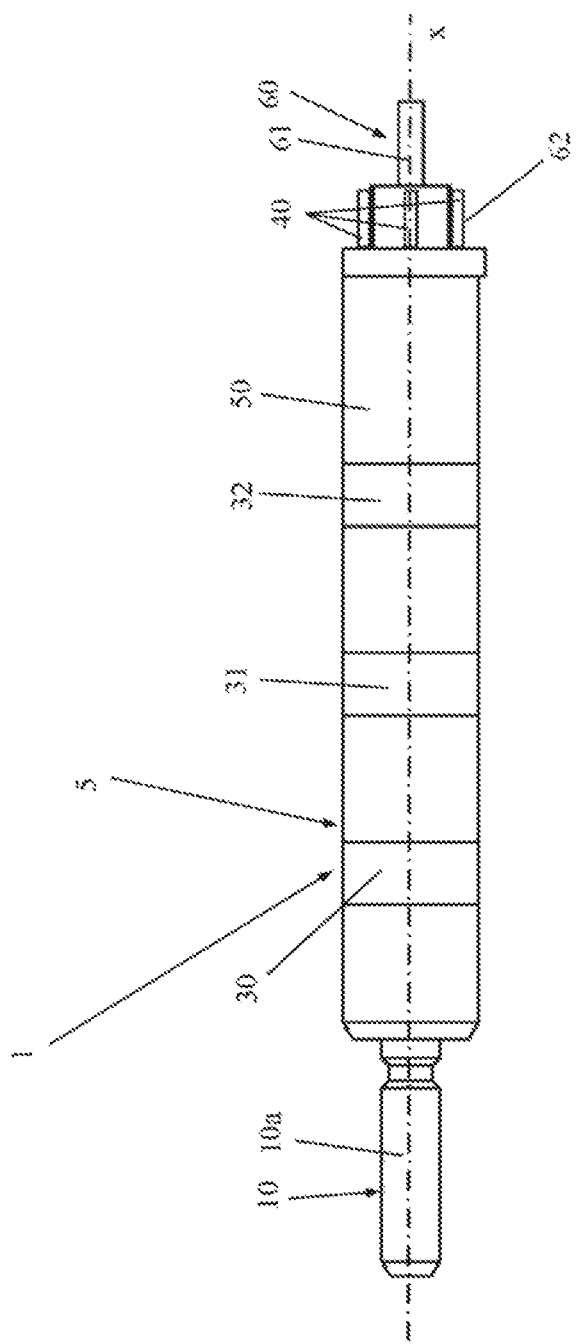
FIG. 1 shows a side view of an embodiment of a plug according to the present invention.

FIG. 1 shows, in conjunction with FIGS. 2 to 5, an embodiment of a plug 1 according to the present invention. The plug 1 has a plug housing 5, which extends along a longitudinal axis x, and a monolithic plug connector 10 extended along the longitudinal axis x and which has a contact portion 10a and a fastening portion 10b connected integrally to the contact portion 10a. The contact portion is used to electrically contact the plug connector 10. To this end the contact portion 10a can be inserted into a correspondingly shaped socket (not shown). By contrast, the fastening portion 10b is cast form-fittingly in the plug housing 5 so that the contact portion 10a protrudes out from the plug housing 5 at a first end 5a of the plug housing 5 in the direction of the longitudinal axis x.

The plug 1 also has three plug contact rings 30, 31, 32, which are arranged coaxially with respect to the longitudinal axis x and which are likewise used to electrically contact the plug 1, wherein each plug contact ring 30, 31, 32 has an outer side 30b, 31b, 32b. The plug contact rings 30, 31, 32 are embedded or cast in the plug housing 5 so that the outer sides 30b, 31b, 32b of the plug contact rings 30, 31, 32 are each arranged in an exposed manner on an outer side 50 of the plug housing 5 and are electrically contactable. Here, the outer sides 30b, 31b, 32b can be formed flush with an outer side 50 of the plug housing 5.

The fastening portion 10b of the plug connector 10 and the plug contact rings 30, 31, 32 are each electrically conductively connected to a first end portion 40a of an associated electrical conductor 40, for example, in each case via a welded connection, which, for example, is produced by means of a laser, wherein each conductor 40 is cast in the plug housing 5 and protrudes out from the plug housing at a second end 5a or an end face 5c of the plug housing 5 via a second end portion 40c. The second end portions 40c of the conductors 40, which are each connected via a middle portion 40b to the corresponding first end portion 40a, each form a contact for electrically contacting the corresponding conductor 40 and thus the plug connector 10 and the plug contact rings 30, 31, 32.

The connection between the fastening portion 10b of the plug connector 10 and the corresponding conductor 40 ensures a non-rotatable connection between the fastening portion 10b and the plug housing 5 following the casting of the plug connector 10 and of the plug connectors 30, 31, 32 and conductors 40 in the plug housing 5.

Furthermore, the fastening portion 10b can have a circumferential recess 10d (see FIG. 2A) so that the plug housing 5 can engage in said recess 10d. The plug connector 10 is hereby better held in the plug housing 5 in the direction of the longitudinal axis x.

Figure 2A:
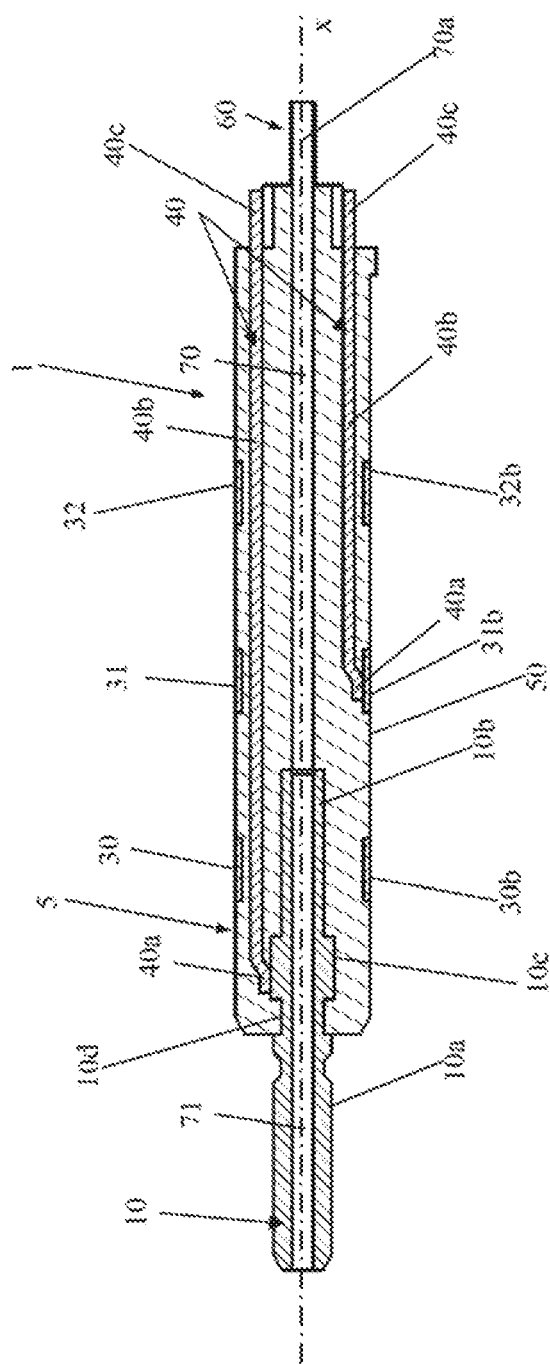
FIG. 2A shows a sectional view of the plug shown in FIG. 1.
Figure 2B:
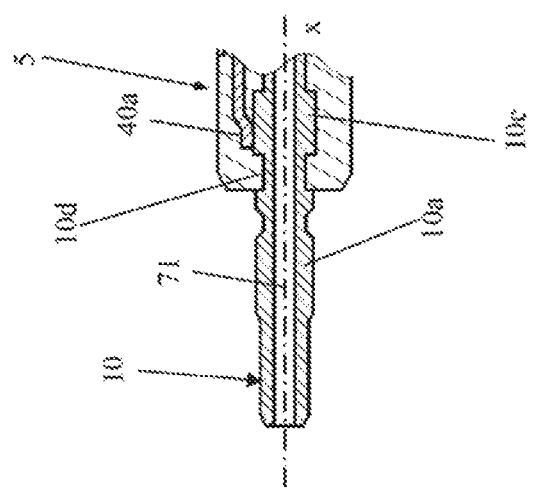
FIG. 2B shows an alternative design of the contact portion of the plug connector.

FIGS. 2A and 2B show two alternative designs for the contact portion 10a, wherein FIG. 2A shows the design of the contact portion 10a of an IS4 plug 1 and FIG. 2B shows the contact portion 10a of a DF4 plug 1.

Figure 5:
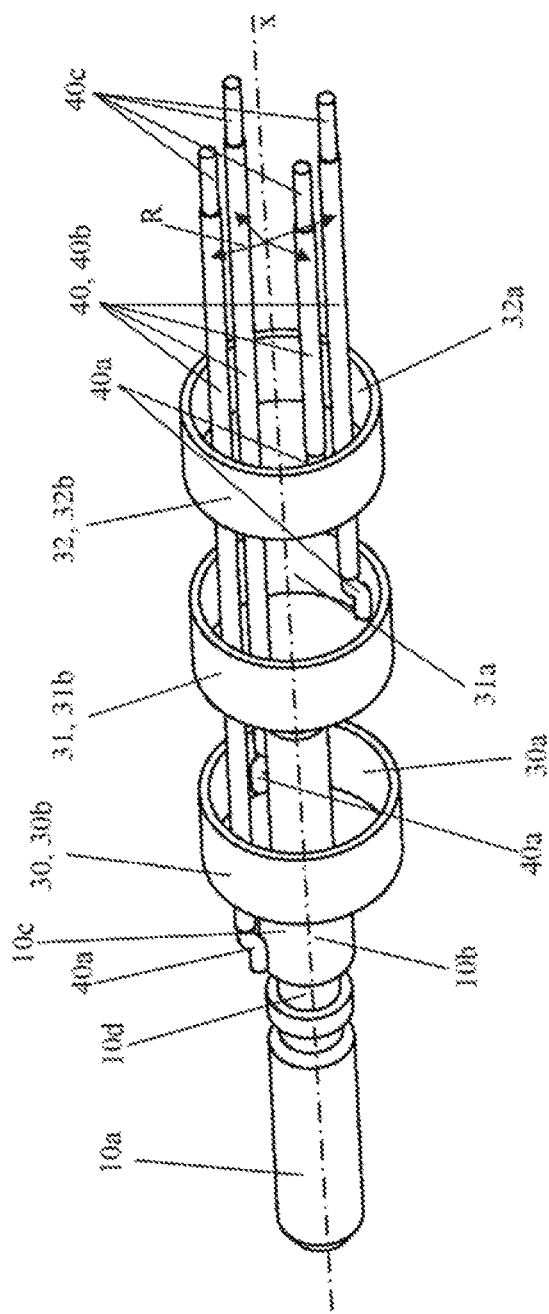
FIG. 5 shows a perspective view of the plug connector of the plug contact rings and of the conductors of the plug shown in FIGS. 1 to 4 without the surrounding plug housing.

As can be seen in particular from FIG. 5, it is preferably provided that the conductors 40 are each arranged further inwardly than the plug contact rings 30, 31, 32 in a radial direction R running perpendicularly to the longitudinal axis x. Here, the first end portion 40a of each conductor 40 is electrically conductively connected to an inner side 30a, 31a, 32a of the associated plug contact ring 30, 31, 32 or to an outer side 10c of the connector portion 10. The first end portions 40a of the conductors 40 can be angled or curved for this purpose, so as to facilitate a connection to the inner side 30a, 31a, 32a of the associated plug contact ring 30, 31, 32 or to the circumferential outer side 10c of the fastening portion 10b of the plug connector 10.

The middle and second end portions 40b, 40c of the electrical conductors 40 extend preferably parallel to the longitudinal axis x, wherein the middle portions 40b and the end portions 40c of the conductors 40 are each arranged at the same distance from the longitudinal axis x in a radial direction R, i.e. are arranged over the same radial circle. This enables simple contacting of all conductors 40 or of the plug connector and the plug contact ings 30, 31, 32 at the second end 5b of the plug housing 5.

The plug contact rings 30, 31, 32 are arranged adjacently along the longitudinal axis x, wherein, in particular, a first plug contact ring 30 extends in the circumferential direction of the plug connector 10 around the fastening portion 10b of the plug connector 10 and around the conductor 40 that is electrically conductively connected via its first end portion 40a to the inner side 30a of the first plug contact ring 30. It is furthermore provided, in particular, that the second plug contact ring 31, which is arranged along the longitudinal axis x between the first plug contact ring 30 and the third plug contact ring 32, extends around those conductors 40 that are electrically conductively connected to the fastening portion 10b of the plug, connector 10, the first plug contact ring 30, or the second plug contact ring 31. It is furthermore provided, in particular, that the third plug contact ring 32 extends around all four conductors 40.

It is also clear from FIG. 5 that the plug connector 10 protrudes via its fastening portion 10b preferably into the first plug contact ring 30, i.e. into an opening defined or surrounded by the first plug contact ring 30, wherein the plug connector ends here in the direction of the longitudinal axis x between the first plug contact ring 30 and the second plug contact ring 31. This advantageously relatively short design of the plug connector 10 in the direction of the longitudinal axis x is made possible by the contacting of the plug connector 10 by means of the associated conductor 40.

It is furthermore preferably provided (see FIG. 2A) that the plug housing 5 surrounds an inner lumen 70, wherein the inner lumen 70 is fluidically connected to a lumen 71 of the plug connector 10. In this way, the plug 1 has a continuous lumen 70, 71, which for example is used to receive a guide wire or a mandrel.

Figure 3:
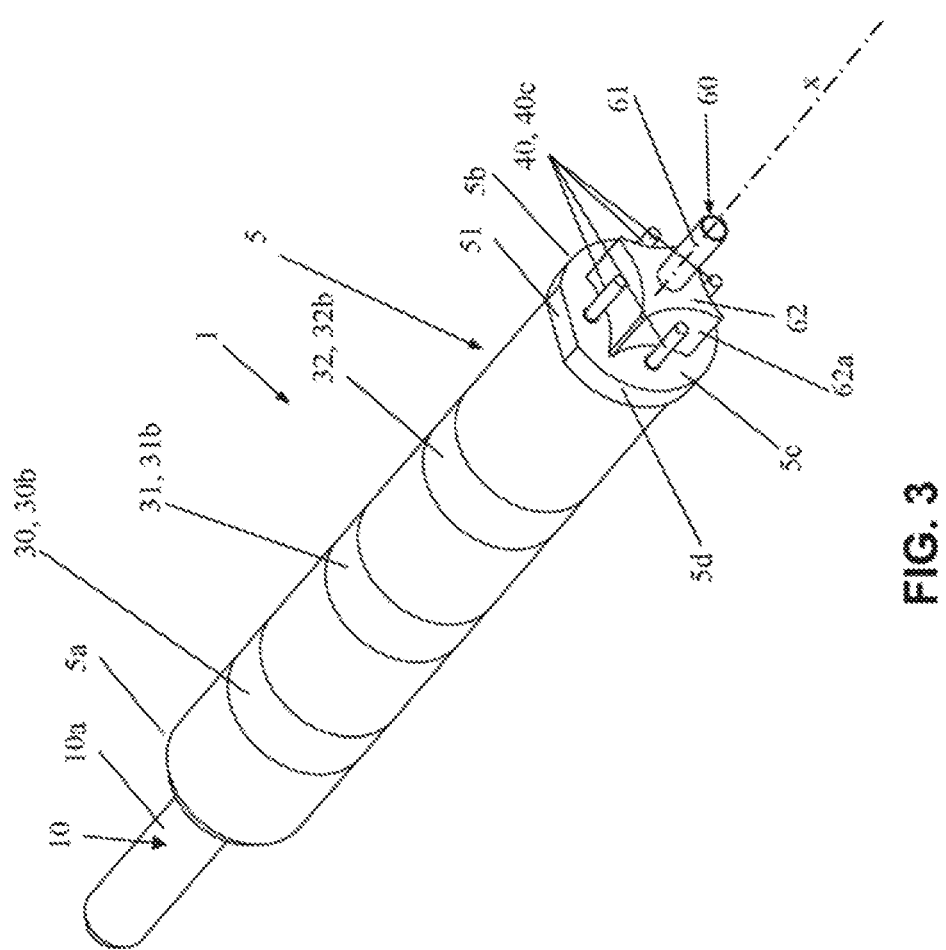
FIG. 3 shows a perspective view of the plug shown in FIGS. 1 and 2.
Figure 4:
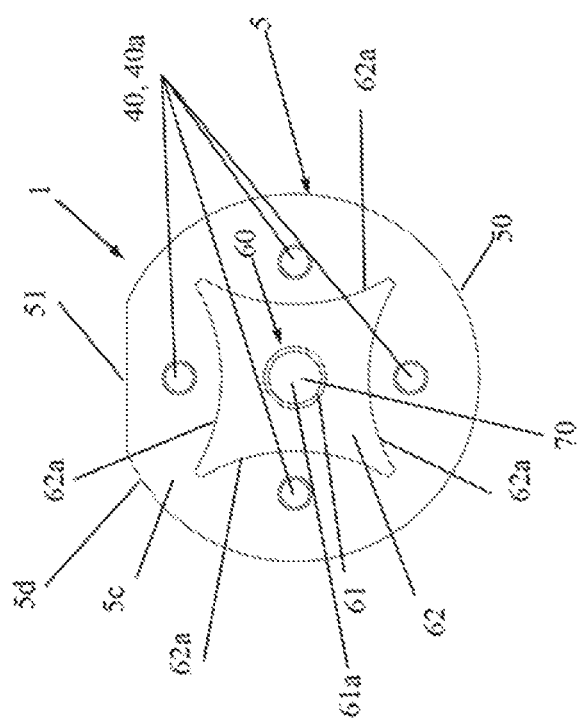
FIG. 4 shows a plan view of the second end or an end face of the plug housing of the plug shown in FIGS. 1 to 3.

Furthermore, the plug housing 5 of the plug 1, as is clear, in particular, from FIGS. 3 and 4, can have a protrusion 60 formed at the second end 5b of the plug housing 5, which protrusion surrounds an end portion 70a of the inner lumen 70. The protrusion 60 can protrude from an end face 5c of the plug housing 5, which faces away from the plug connector 10. The protrusion 60 is designed in particular to protect the contacts of the conductors 40 provided at the end portions 40c against a liquid in the lumen 70 of the plug 1 or plug housing 5.

The protrusion 60 can have a cylindrical first portion 61, which, at the end face, has an opening 61a, via which the inner lumen 70 is accessible. Furthermore, the protrusion 60 has a second portion 62 connected to the first portion 61, wherein the second portion 62 has four concave side walls 62a, wherein each concave side wall 62a is opposite an end portion 40c or contact of a conductor 40. Said side walls 62a of the second portion 62 can alternatively also be straight or convex.

Lastly, the plug 1 can have a coding 51, which is used to distinguish between the conductors 40 so that the contacts 40c thereof can be correctly contacted. The coding 51 can be formed here at a circumferential edge 5d of the end face 5c of the plug housing 5 from which said protrusion 60 of the plug 1 protrudes. The coding 51 is preferably formed by a flattened portion of the plug housing 5 at said edge 5d. Alternatively, the coding 51 of the plug 1 can also be formed by a groove or by an elevation, for example, in the form of a point, at said edge 5d.

In order to produce the plug 1, it can be provided in accordance with an embodiment of the present invention that the plug connector 10 and also the three plug contact rings 30, 31, 32 are arranged in a casting mold, wherein the plug housing 5 is formed by introducing a casting material into the casting mold so that the fastening portion 10b of the plug connector 10 is surrounded form-fittingly by the casting material and the contact portion 10a protrudes out from the plug housing 5 in the direction of the longitudinal axis x at a first end 5a of the plug housing 5.

The positioning of the plug connector 10 with respect to the plug contact rings 30, 31, 32 during the casting, in particular injection molding, of the plug housing 5 is evident from FIG. 5. FIG. 5 furthermore shows the position of the conductors 40 connected to the plug connector 10 or to the plug contact rings 30, 31, 32, which conductors are cast in the plug housing 5 together with the plug connector 10 and the plug contact rings.

The lumen 70 of the plug housing 5 can be formed by inserting an appropriate core into the casting mold, which core can be removed once the plug housing 5 has been formed.

The casting material can be, for example, PEEK or another plastic, wherein the hardness of the particular plastic material is greater than 75 Shore D, and wherein the particular plastic material has a mean roughness (Ra) that is less than 0.8 μm.

The present invention advantageously makes it possible to produce a simple and economical plug housing, wherein in particular simple electrical attachment to the plug is possible, since all electrical contacts of the conductors are identically contactable (on account of the positioning over the same radial circle). This has proven to be favorable in respect of manufacture and cost-reducing. Furthermore, there is no need for additional anti-twist means of the plug connector, and play of the plug connector (pin play) is largely avoided since the plug connector is fixedly embedded in the plug housing. Furthermore, there is no axial offset between the plug connector and the plug housing, since the parts are fixedly connected to one another and there is no need for separate assembly. Lastly, there is no need for any additional components in order to seal off the inner lumen.

It will be apparent to those skilled in the art that numerous modifications and variations of the described examples and embodiments are possible in light of the above teachings of the disclosure. The disclosed examples and embodiments may include some or all of the features disclosed herein. Therefore, it is the intent to cover all such modifications and alternate embodiments as may come within the true scope of this invention, which is to be given the full breadth thereof.

Additionally, the disclosure of a range of values is a disclosure of every numerical value within that range, including the end points.

We claim:

1. A method for producing a plug, wherein a plug connector and three plug contact rings are arranged in a casting mold, wherein the plug connector extends along a longitudinal axis and has a contact portion and a fastening portion connected integrally to the contact portion, and wherein a plug housing is formed by introducing a casting material into the casting mold so that the fastening portion is surrounded form-fittingly by the casting material and the contact portion protrudes out from the plug housing at a first end of the plug housing in the direction of the longitudinal axis.

2. The method according to claim 1, wherein the plug contact rings each have an outer side, wherein the plug housing is formed by introducing the casting material into the casting mold so that the outer sides of the plug contact rings are each arranged in an exposed manner on an outer side of the plug housing so that the outer sides of the plug contact rings are electrically contactable.

3. The method according to claim 1, wherein, the fastening portion and the three plug contact rings are electrically conductively connected to a first end portion of an electrical conductor each prior to the introduction of the casting material into the casting mold, wherein each conductor has a second end portion, which forms a contact of the plug in order to electrically contact the corresponding conductor.

4. The method according to claim 3, wherein the tour conductors are enclosed in the plug housing by the introduction of the casting material into the casting mold, so that the second end portions of the conductors protrude out from the plug housing at a second end of the plug housing.

5. The method according to claim 4, wherein the second end portion of each conductor extends along the longitudinal axis, and wherein the second end portions each are arranged at the same distance from the longitudinal axis in a radial direction running perpendicularly to the longitudinal axis.

6. The method according to claim 3, wherein each conductor electrically conductively connected to a plug contact ring is electrically conductively connected via the first end portion to an inner side of the plug contact ring.

7. The method according to claim 1, wherein in order to form a protrusion of the plug housing at the second end of the plug housing, which protrusion is extended along the longitudinal axis, and/or in order to form an inner lumen of the plug housing extended along the longitudinal axis, a core is arranged in the casting mold prior to the introduction of the casting material into the casting mold.

8. The method according to claim 1, wherein the plug housing is cast from the casting material such that the plug housing has a coding for distinguishing between the conductors.

9. The method according to claim 1, wherein the casting material is one of the following materials: PEEK or another plastic, wherein the particular plastic material has a hardness that is greater than 75 Shore D.

10. A plug, produced by a method according to claim 1.

* * * * *